United States Patent [19]

Schneider et al.

[11] Patent Number: 4,477,569

[45] Date of Patent: Oct. 16, 1984

[54] PENTOSE FERMENTATION WITH SELECTED YEAST

[75] Inventors: Henry Schneider, Nepean; Ryszard Maleszka, Ottawa, both of Canada; Patrick Y. Wang, Hong Kong, Hong Kong; Ivan A. Veliky; Yui-Kwok Chan, both of Ottawa, Canada

[73] Assignee: Canadian Patents & Development Limited, Ottawa, Canada

[21] Appl. No.: 349,905

[22] Filed: Feb. 18, 1982

[51] Int. Cl.³ .......................... C12P 7/06; C12N 1/16; C12R 1/645

[52] U.S. Cl. .................................... 435/161; 435/255; 435/911

[58] Field of Search .................................. 435/99, 161

[56] References Cited

U.S. PATENT DOCUMENTS 4,102,745  7/1978  Thompson et al. .............. 435/99 X
4,359,534 11/1982  Kurtzman et al. .................. 435/161

Primary Examiner—Ferris H. Lander
Attorney, Agent, or Firm—Alan A. Thomson

[57] ABSTRACT

It has been found possible to ferment the pentose D-xylose directly to ethanol with the selected yeast *Pachysolen tannophilus*. At least an initial aerobic stage is desirable. Improved yields have been obtained when the yeast cells are recycled continually at high cell densities. Fermentation of D-galactose and other hexoses along with D-xylose has been found possible with selected strains or mutants.

10 Claims, 2 Drawing Figures

PENTOSE FERMENTATION WITH SELECTED YEAST

This invention is directed to the fermentative conversion into ethanol of the aldopentose D-xylose, which occurs in many natural products or byproducts. The yeast *Pachysolen tannophilus* has been found to effect this conversion in good yields. A selected mutant can convert several biomass sugars including xylose in the same mixture into ethanol.

BACKGROUND AND PRIOR ART

Because of the interest in producing ethanol from the five as well as the six carbon sugars in biomass, it would be useful to have yeasts which ferment both sugar types. However, while many yeasts ferment hexoses, they are usually considered to be unable to ferment aldopentoses. Several species ferment a ketopentose (P. Y. Wang, C. Shopsis and H. Schneider, Biochem. Biophys. Res. Comm., 94, p. 248–254, 1980), but biomass pentoses are aldopentoses, e.g. D-xylose.

A process has been described which depends on the addition of glucose isomerase to culture media containing D-xylose to form D-xylulose, which is then converted to ethanol by several yeasts (Wang, Johnson and Schneider, Biotechnology Letters 1980, Vol. 2(6), p. 279–284). A similar process has been reported by others (C.-S. Gong et al, Applied and Environmental Microbiology, Vol, 41, No. 2, Feb. 1981, p. 430–436). This process is limited by the requirement of relatively long culturing times and the high cost of enzyme.

One report has been noticed where some D-xylose was converted to ethanol by *Candida tropicalis* (H. Karczewska, Compt. Rend. Lab., Carlsberg, 1959, Vol. 31, p. 251-8). The yields of ethanol were unclear.

SUMMARY OF THE INVENTION

The yeast *Pachysolen tannophilus* has been found to produce ethanol directly from D-xylose. The conversion is enhanced by the presence of air at least initially. The invention includes a method of producing ethanol directly from D-xylose which comprises (a) inoculating a growth-supporting medium containing D-xylose with the yeast *Pachysolen tannophilus*, (b) providing access of air or oxygen to the medium at least for an initial stage, and (c) allowing growth and accumulation of ethanol to occur. Preferably, the spent medium and yeast cells are separated and the cells recycled to ferment fresh xylose-containing media. Desirably the cells will be recovered and recycled continually. Recycling of the cells can be facilitated by immobilizing the cells on a substrate or in a gel or separate phase. Where the media being fermented contain galactose as well as D-xylose (and other sugars), a mutant of the yeast has been selected which can ferment all or most of these sugars to ethanol.

DETAILED DESCRIPTION AND PREFERRED EMBODIMENTS

Figure 1:
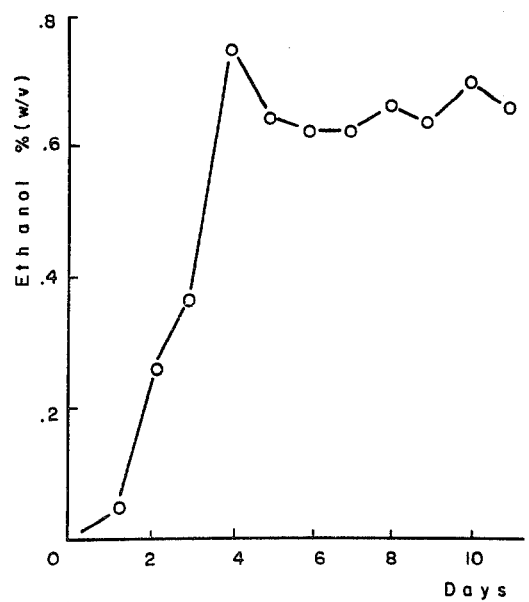
FIG. 1 is a graph showing ethanol produced by recycled cells of *P. tannophilus*. Each point represents the concentration of ethanol accumulated in 24 hrs. after resuspension in fresh medium.

The media fermented can be any containing a suitable nitrogen and vitamin source for yeasts and a carbon source comprising D-xylose, on which the yeast will grow. Preferably, the concentration of D-xylose is withing the range from about 0.5 to about 5% w/v, most preferably about 2%.

Various strains or mutants of the yeast *Pachysolen tannophilus* can be used. Strains available from culture collections, e.g. NRRL-Y-2460, -2461, -2462 and -2463, may be used. It has been found advantageous to select strains or mutants most suitable for the particular mixture being fermented. One mutant has been selected which is able to convert to ethanol, D-galactose and other hexoses as well as D-xylose in the same mixture. This mutant is being maintained in the culture collection, Div. of Biol. Sciences, National Research Council of Canada, Ottawa, under the designation NRCC-PTXG-1.

Ethanol production has been found to be enhanced by at least one of (1) exposure to air or oxygen at least for an initial stage, and (2) recycling of cells at high cell densities. Aerobic conditions can be provided for the entire fermentation or for only an initial growth stage, such as 4–8 hrs. To effect recycling of the cells, they are separated from the spent medium (e.g. by centrifugation or filtration, or by having them immobilized in a readily separable phase) and contacted with fresh medium. Preferably the cells densities with recycling are above about 7.5 mg dry wt. per ml of culture. Preferably, the fermentation temperature is about 30°-37° C.

The yeast cells can be immobilized, for example, in a gel such as an alginate, a polyacrylamide or a carrageenan. The alginate may be for instance, a calcium alginate or an alginate cross-linked with polyethyleneimine.

The following examples are illustrative.

EXAMPLE 1

Alcohol production was measured under four different conditions of aeration. (1) Aerobic: 6 mls of culture in 150×16 mm loosely capped, screw-cap test tubes, rotated at 100 rpm at an angle of 30° from the horizontal. (2) Semi-aerobic: these differed from those denoted aerobic in the use of a larger culture volume, 12 ml, and a shorter tube, 125 mm. Partly, because of the resulting longer column of culture and the inefficiency of the rotation method in stirring such columns, the time-average amount of $O_2$ available per cell was expected to be smaller in the 12 ml than in the 6 ml cultures. (3) Finite air supply: 5 ml in a 120 ml serum bottle sealed with a butyl rubber cap and shaken at 150 rpm. The amount of $O_2$ available was ~55% of that required to completely oxidize the D-xylose when present as a 2% solution. (4) Anoxic: 4.5 ml in tightly sealed, 5.0 ml screw-cap vials, which were mixed by inversion at 30 rpm. Inocula were grown aerobically in 0.67% yeast nitrogen base plus 2% D-xylose. Incubations were at 30° C. Optical density was measured at 600 mm in the culture tubes or vials. The D-xylose used was chromatographically pure. Ethanol was measured by gas chromatography and its identification confirmed by mass spectrometry.

Alcohol production by *P. tannophilus* NRRL Y-2460 after 3 days on 0.67% yeast nitrogen base plus 0.4% casamino acids and 2% D-xylose is summarized in Table 1. The deliberate addition of air is seen to have enhanced alcohol production. In addition, there were differences in the amount of alcohol produced by the aerobic cultures, depending on the particular conditions of aeration. The highest concentration found, 0.53%, corresponds to a yield of 52%, computed assuming that the D-xylose is catabolized to D-xylulose 5-phosphate, then to glucose 6-phosphate, after which the normal glycolytic pathway is followed. This computed yield was also a minimum, since all of the D-xylose was assumed to have been consumed.

TABLE 1

Optical density and medium alcohol concentration under various conditions of aeration

| | Aerobic | Semi-aerobic | Finite air supply | Anoxic |
|---|---|---|---|---|
| optical density* | 1.2 | 0.9 | n.d. | 0.07 |
| alcohol conc. (%) | 0.38 | 0.53 | 0.25 | <0.03 |

*Optical density at inoculation was 0.04 to 0.06

After 4 days, the alcohol concentration in the aerobic and semi-aerobic cultures decreased, only traces being found after 9 days. This behavior is attributable largely to the ability of *P. tannophilus* to assimilate ethanol.

Although some growth and alcohol production occurred eventually in the anoxic cultures, such cultures were not studied systematically after the first 3 days, attention being focussed on the prominent role played by air on ethanol formation.

Further tests have shown that the rate of ethanol production can be increased and that continuous aerobic conditions are not necessary with cell recycling at high cell densities or with immobilized cells (as in the following example).

EXAMPLE 2

Yeast Recycling. Cells of *P. tannophilus* NRRL Y-2460 were inoculated to an O.D. of 0.05 in a volume of 100 mls in a 250 ml Erlenmeyer flask and grown aerobically. The medium was 0.67% yeast nitrogen base plus 2% xylose, and was sterilized by filtration. The culture flask was shaken on a gyrotatory shaker at 150 rpm at 30° C. At 24 hr intervals, the cells were separated by centrifugation and put back into 100 ml of fresh medium. Optical density (600 m$\mu$) and medium ethanol concentration were measured just prior to centrifugation. Ethanol was determined by gas chromatography.

The aeration requirement was determined by transferring 10 ml aliquots into screw-capped test tubes immediately after resuspending the cells in fresh medium. These tubes were then loosely capped, to provide the semi-aerobic conditions described previously or sealed tightly, to prevent entry of air. They were then rotated at ~30 rpm. Ethanol concentration was measured after 24 hrs.

Yeast Immobilization. *P. tannophilus* was immobilized in Ca-alginate gels using the procedure described by I. A. Veliky and R. E. Williams, Biotechnology Letters, Vol. 3(6), p. 275-280, 1981. Two hundred beads were suspended in 10 ml of medium in a 50 ml Erlenmeyer flask and kept stationary at 30° C. At 24 hr intervals, a sample was removed for ethanol determination, and the medium was then drained off and replenished. The medium consisted of 0.67% yeast extract, 20 mM CaCl$_2$.2H$_2$O plus 2% D-xylose. The pH was adjusted to 5.0 before autoclaving.

In the first 2 days of the recycling procedure, using cell suspensions, the optical density increased to 1.2 and then slowly increased to 1.4 in the course of 11 cycles, after which the experiment was terminated. The ethanol concentration after the first day was 0.075% (FIG. 1). It increased to 0.75% after the fourth and remained in the 0.62–0.70% range for the remainder of the experiment. Thus, recycled cells at an O.D. ≥1.2 can produce a 0.62–0.7% solution of ethanol from 2% D-xylose in 24 hours.

Test results indicate that recycled cells in suspension culture do not require continuous aeration to be able to ferment D-xylose almost as rapidly as with aeration. Aliquots of a freshly recycled culture (5th cycle) produced similar amounts of ethanol in a loosely stoppered flask (0.75%) as in a loosely capped test tube (0.72%) after 24 hours at the same temperature (Table 2). However, in a sealed tube, the ethanol concentration, 0.69%, was only slightly lower than in that which was loosely capped.

TABLE 2

Ethanol produced in 24 hours by recycled cells in a loosely-capped flask, a loosely-capped tube, and a closed tube

| | Ethanol Concentration % (w/v) | | |
|---|---|---|---|
| Temperature °C. | Flask | Loosely-capped tube | Closed tube |
| 30 | 0.75 | 0.72 | 0.69 |
| 37 | | 0.79 | 0.71 |

Increasing temperature to 37° C. increased the amount of ethanol found after 24 hours (Table 2). The increase corresponds to about 10% in a loosely-capped tube, and about 5% in a closed tube. The value of 0.79% obtained at 37° C. with a loosely-capped tube represents a considerable improvement over the 0.53% obtained after 3 days in Ex. 1. The value of 0.79% corresponds to a theoretical yield of 78% which is probably a minimum. All of the D-xylose was assumed to have been converted to ethanol, while xylitol has been found in some culture media.

The higher ethanol concentration at 37° C. than at 30° C. is probably due to more rapid fermentation, rather than to other factors such as less byproduct formation. When alcohol concentration was followed for longer periods of time, the values at 30° C. increased after 60 hours to those found at 37° C. after 24 hours.

Figure 2:
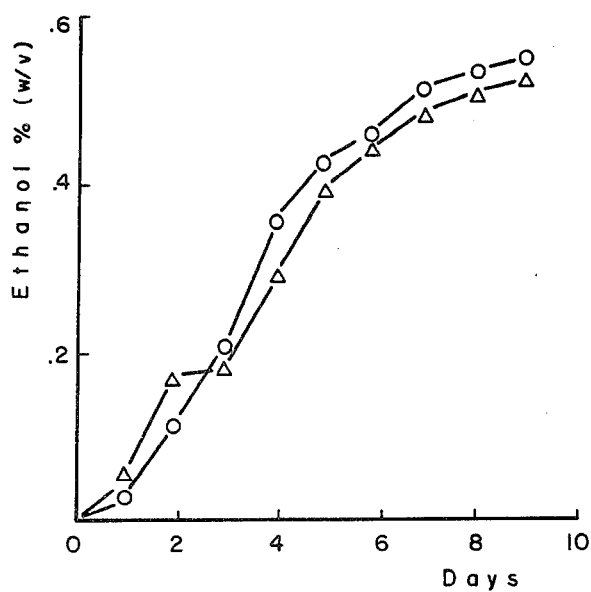
FIG. 2 is a graph showing ethanol produced by immobilized cells of *P. tannophilus*. Open circles represent concentrations accumulated in 24 hrs. on a drain and refill basis in vessels with a foam plug exposed to the atmosphere. Open triangles represent concentrations accumulated in 24 hrs. in vessels kept in an anaerobic enclosure.

With immobilized *P. tannophilus,* the amount of ethanol produced in a 24 hr period increased with each drain and refill cycle (FIG. 2). After the 9th cycle, when the experiment was terminated, the alcohol concentration produced in 24 hours from 2% D-xylose was 0.55%. The rate of alcohol production at 37° C. also exceeded that at 30° C. for the first 72 hours.

Immobilized cells of *P. tannophilus* do not require continuous aeration to produce ethanol. This was demonstrated by keeping cultures in an atmosphere of H$_2$ and CO$_2$ in a Gas-Pak [trademark] jar. Under these conditions, results were essentially similar to those with the flasks in air (FIG. 2).

It should be understood that the conditions used in these tests have not been optimized. It is expected that yields would be further improved under more optimized conditions.

EXAMPLE 3

The common strains of *P. tannophilus* were found to ferment D-galactose to ethanol at high cell densities (above about 7 mg dry wt/ml) with cell recycling (ethanol yield about 75% of theoretical). However, if other sugars, such as D-glucose, D-mannose or D-xylose are present, the D-galactose is not fermented significantly.

Mutants were prepared by chemical mutagenesis with ethyl methanesulfonate of NRRL Y-2460. After screening the yeast cell mutants formed for maximum growth on D-galactose containing media, we have isolated the mutant NRCC-PTXG-1 which is able to ferment four of the five major biomass sugars in mixtures, i.e. D-glucose, D-mannose, D-galactose and D-xylose. The fifth (L-arabinose) apparently was not fermented.

As an example, an aqueous mixture simulating the sugar composition of a spent sulfite liquor, was fermented with this mutant. The carbon source of the mixture consisted of glucose 0.61% w/v, mannose 1.36%, galactose 0.91%, xylose 0.76%, and arabinose 0.21% (total 3.85%). Using recycled mutant cells at a cell density of above about 7.5 mg dry wt per ml, after fermentation at 30° C., for 6 hrs. under aerobic conditions followed by 18 hrs anaerobic, the ethanol concentration obtained was 1.66% (which corresponds to 91.3% of the theoretical yield). Analysis showed that all sugars, except arabinose, had been fermented. Even higher yields are possible with further optimization of conditions and medium.

We claim:

1. A method of producing ethanol directly from a substrate comprising D-galactose and D-xylose, which comprises:
   (a) screening and selecting *Pachysolen tannophilus* having the identifying characteristics of NRCC-PTXG-1 or mutants thereof which can ferment at least said two sugars to ethanol, concurrently,
   (b) inoculating a growth-supporting medium containing said substrate with the selected mutant,
   (c) providing access of air or oxygen to the medium at least for an initial stage,
   (d) allowing growth and accumulation of ethanol to occur,
   (e) separating the medium from the yeast cells and recovering ethanol, and
   (f) recycling the yeast cells to ferment fresh medium in (b).

2. The method of claim 1 wherein the cells are separated and recycled continually.

3. The method of claim 2 wherein ethanol is recovered from media fermented with recycled cells until the highest ethanol concentration is achieved.

4. The method of claim 1 wherein the cells being recycled are immobilized.

5. The method of claim 4 wherein the cells are immobilized in a gel of the alginate type.

6. The method of claim 1 wherein the cells are separated and recycled at about 24 hour intervals.

7. The method of claim 1 wherein the fermentation temperature is about 30°–37° C.

8. The method of claim 1 wherein the fermentations for ethanol production are run aerobically for the first 4–8 hours, and anaerobically for the remainder of the fermentations.

9. The method of claim 8 wherein the cell densities are above about 7.5 mg dry wt. per ml of culture for ethanol production.

10. The method of claim 1 wherein the substrate comprises a spent sulfite liquor.

* * * * *